(12) United States Patent
Wang

(10) Patent No.: US 11,713,957 B2
(45) Date of Patent: Aug. 1, 2023

(54) MEASURING TAPE FOR MEASURING THE SIZE OF LIMBS OR WAISTS

(71) Applicant: Shenzhen Hanhou Technology Co., Ltd., Shenzhen (CN)

(72) Inventor: Yongbin Wang, Shenzhen (CN)

(73) Assignee: Shenzhen Hanhou Technology Co., Ltd., Shenzhen (CN)

( * ) Notice: Subject to any disclaimer, the term of this patent is extended or adjusted under 35 U.S.C. 154(b) by 0 days.

(21) Appl. No.: 17/668,375

(22) Filed: Feb. 9, 2022

(65) Prior Publication Data

US 2023/0204336 A1 Jun. 29, 2023

(51) Int. Cl.
*G01B 5/02* (2006.01)
*G01B 3/1048* (2020.01)

(52) U.S. Cl.
CPC ........... *G01B 5/025* (2013.01); *G01B 3/1048* (2020.01)

(58) Field of Classification Search
CPC ................. G01B 5/025; G01B 3/1048; G01B 2003/1033
USPC ................. 33/759, 758, 761, 512, 511, 555.4
See application file for complete search history.

(56) References Cited

U.S. PATENT DOCUMENTS

| | | | | |
|---|---|---|---|---|
| 2,129,582 A * | 9/1938 | Israel Johansson | ... | G01B 5/025 242/385.4 |
| 4,875,296 A * | 10/1989 | Holzmeister | .......... | G01B 3/004 33/2 R |
| 5,193,287 A * | 3/1993 | Coulter | .................. | A61B 5/107 33/511 |
| 5,367,785 A * | 11/1994 | Benarroch | ............ | E05B 67/006 33/760 |
| 5,619,804 A * | 4/1997 | Vogt | ..................... | G01B 3/1084 33/759 |
| 6,640,460 B1 * | 11/2003 | Nabarro | ................... | A41H 5/01 33/759 |
| 6,817,110 B2 * | 11/2004 | Bohnengel | ........... | G01B 3/1056 33/759 |
| 7,146,743 B2 * | 12/2006 | Oura | ..................... | G01D 5/363 33/555.4 |
| 9,228,817 B2 * | 1/2016 | Towns | ................... | G01B 5/025 |
| 11,147,475 B2 * | 10/2021 | Harfouche | ........... | G01B 3/1041 |
| 11,419,522 B2 * | 8/2022 | Bassez | ................ | G01B 3/1084 |
| 2011/0258869 A1 * | 10/2011 | Bittkowski | ............ | A61B 5/107 356/625 |
| 2022/0104727 A1 * | 4/2022 | Harfouche | ............. | G01B 5/025 |

FOREIGN PATENT DOCUMENTS

CN 212112546 U * 12/2020

* cited by examiner

*Primary Examiner* — Christopher W Fulton
(74) *Attorney, Agent, or Firm* — Rahman LLC

(57) ABSTRACT

A measuring tape for measuring the size of limbs or waists is provided with a tape head capable of being stably inserted into a positioning hole during measurement and being automatically ejected out of the positioning hole after measurement, and includes a shell, and a cavity formed in the shell and used for receiving a flexible rule. An elastic switch assembly for clamping the tape head in the positioning hole is disposed at a position, close to the positioning hole, in the cavity. The elastic switch assembly and a leaf spring are disposed in the positioning hole, allowing the tape head to be inserted thereinto, in the shell, such that the tape head can be stably disposed in the positioning hole after being inserted into the positioning hole, and will not slide out of the positioning hole when users observe measure data.

5 Claims, 6 Drawing Sheets

MEASURING TAPE FOR MEASURING THE SIZE OF LIMBS OR WAISTS

BACKGROUND OF THE INVENTION

1. Technical Field

The invention relates to a flexible measure tape, in particular to a measure tape for measuring the size of limbs or waists of human bodies.

2. Description of Related Art

A measure tape is generally used by people to measure the size of their waist, arms or legs in time. A columnar tape head is disposed at the front end of the measure tape, and a positioning hole is formed in one side of a tape shell. When measuring the size of a certain part, users hold the tape shell with one hand and hold the tape head with the other hand to pull a flexible rule out and wind it around the part to be measured (such as the legs, the arms or the waist), and then the users insert the tape head into the positioning hole, such that one hand of the users are freed to turn the flexible rule to observe the measure value. After measurement, the tape head is pulled out of the positioning hole, and a button on the tape shell is pressed to automatically withdraw the flexible rule into a cavity of the shell.

Although the measure tape of such a structure can be used by users for self-measurement, it has the following defects:

1. After the tape head is inserted into the positioning hole, users have to pay careful attention when turning the flexible rule to observe the measure value, otherwise the tape head may automatically slide out of the positioning hole.

2. After measurement, users need to pull the tape head out of the positioning hole by hand.

BRIEF SUMMARY OF THE INVENTION

The technical issue to be settled by the invention is to provide a measure tape for measuring the size of limbs or waists, which is provided with a tape head capable of being stably disposed in a positioning hole during measurement and capable of being automatically ejected out of the positioning hole after measurement.

The technical solution adopted by the invention to settle the above-mentioned technical issue is as follows:

The invention provides a measure tape for measuring the size of limbs or waists, comprising a shell, and a cavity formed in the shell and used for receiving a flexible rule, wherein the shell consists of a top cover and a base, a button for withdrawing the flexible rule into the cavity is disposed on the top cover, a tape head is disposed at an outer end of the flexible rule, the tape head is inserted into a positioning hole in a side, opposite to a tape outlet, of the shell after being held by hand to be pulled out by a desired length via the tape outlet of the shell, an elastic switch assembly for clamping the tape head in the positioning hole is disposed at a position, close to the positioning hole, in the cavity.

The elastic switch assembly consists of a support plate, a toggle and a compression spring, wherein the support plate is disposed in the cavity and is located behind the positioning hole, the toggle consists of a handle, a chuck and a spring plunger which are of an integrated structure, a key hole is formed in the shell on one side of the positioning hole, the handle is disposed outside the key hole, the chuck and the spring plunger are disposed in the cavity, the chuck is a curved chuck, the center of curvature of the chuck is located behind the positioning hole, a front end of the spring plunger is connected to a back side of the chuck, a rear end of the spring plunger penetrates through and disposed in a through hole formed in the support plate, and the compression spring is disposed around the spring plunger and is located between the support plate and the chuck.

The elastic switch assembly consists of a support plate, a key and a compression spring, wherein the support plate is disposed in the cavity and is located behind the positioning hole, the key consists of a press hood, a chuck plate and a spring plunger which are of an integrated structure, a key hole is formed in the shell on one side of the positioning hole, an outer end face of the press hood is a closed face, an inner end face of the press hood is an open hollow cylinder, an annular protrusion is disposed on a peripheral wall of the press hood, a portion between the protrusion and the outer end face of the press hood penetrates through the key hole to be disposed outside the shell, the spring plunger is disposed an inner surface of an outer end in the press hood, the compression spring is disposed around the spring plunger and is located between the inner surface of the outer end in the press hood and an inner plate of the support plate, the chuck plate is a curved plate, and the center of curvature of the chuck plate is located on one side of the positioning hole.

A leaf spring for applying an outward elastic force to the tape head inserted into the positioning hole is disposed at the bottom of the positioning hole.

The tape head is shaped like a dumbbell which becomes larger gradually from the middle to two ends.

Compared with the prior art, the measure tape of the invention has the following beneficial effects: the elastic switch assembly and the leaf spring are disposed in the positioning hole, allowing the tape head to be inserted therein, in the shell of the measure tape, such that the tape head can be stably disposed in the positioning hole after being inserted into the positioning hole, and will not slide out of the positioning hole when users turn the tape rule to observe a measure value. When the tape head needs to be taken out after measurement, the users just need to trigger the elastic switch assembly, and then the tape head can be automatically ejected out of the positioning hole. The measure tape is convenient to use.

Figure 1:
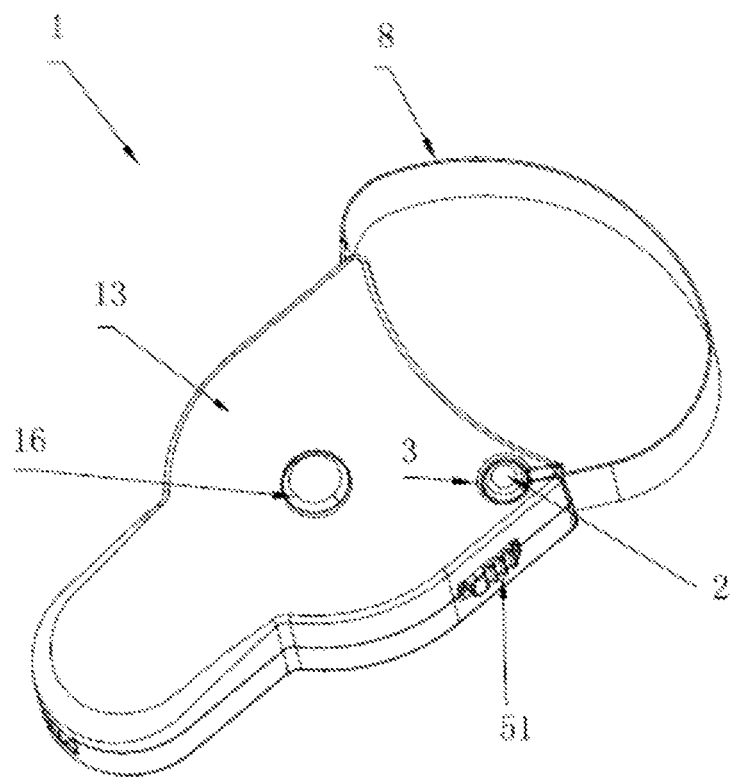
FIG. 1 is an external view of a measure tape according to Embodiment 1 of the invention.
Figure 2:
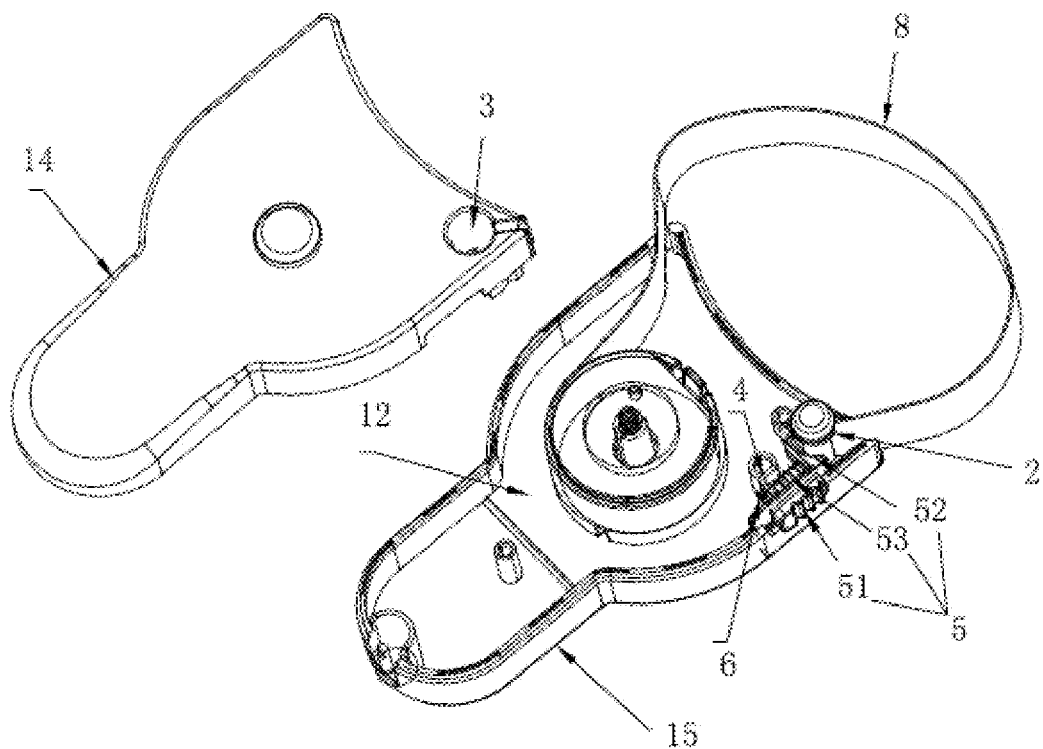
FIG. 2 is a schematic diagram of the measure tape in FIG. 1 after a top cover is opened.
Figure 3:
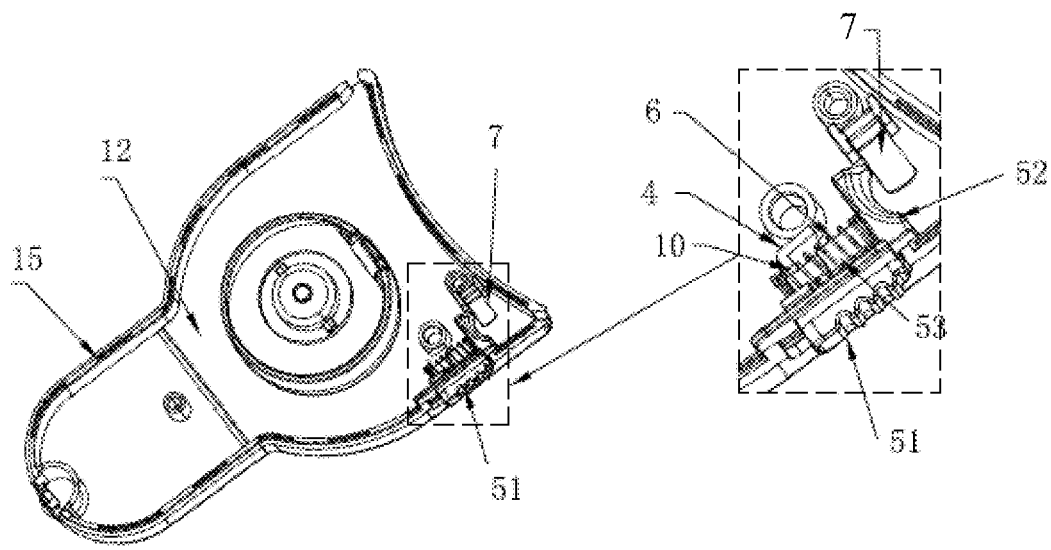
FIG. 3 is a schematic diagram of the measure tape in FIG. 2 after a tape rule is disassembled.
Figure 4:
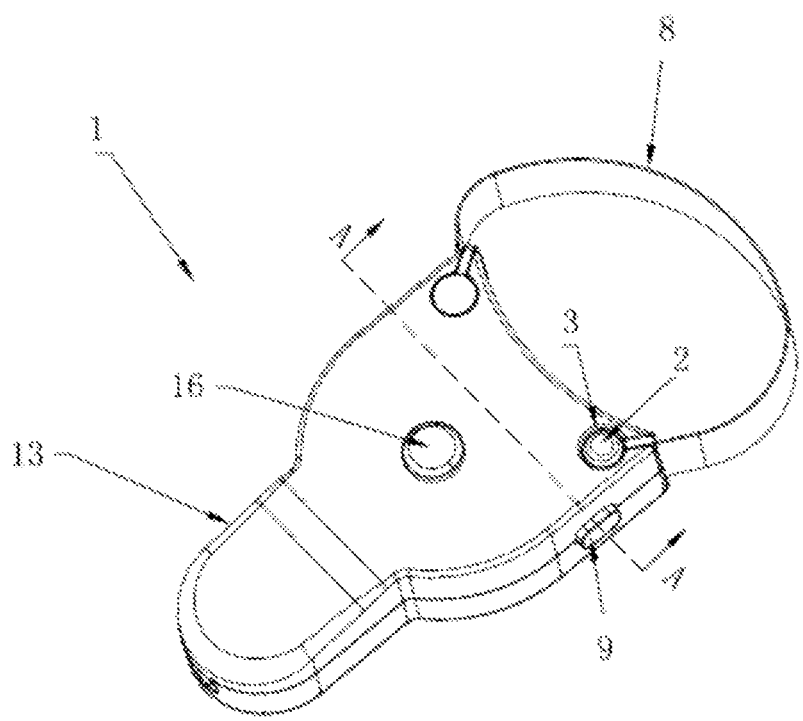
FIG. 4 is an external view of a measure tape according to Embodiment 2 of the invention.
Figure 5:
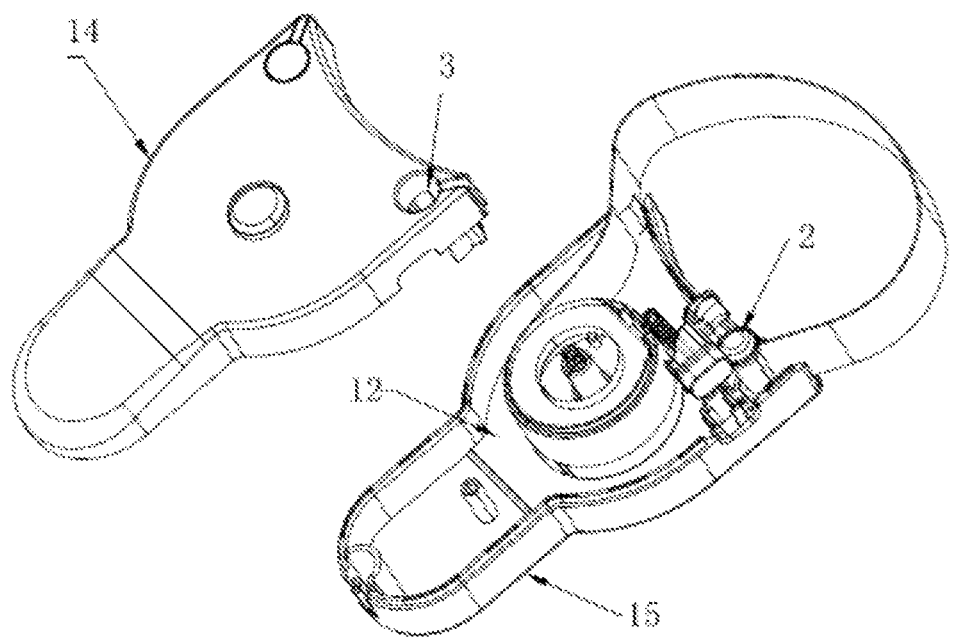
FIG. 5 is a schematic diagram of the measure tape in FIG. 4 after a top cover is opened.
Figure 6:
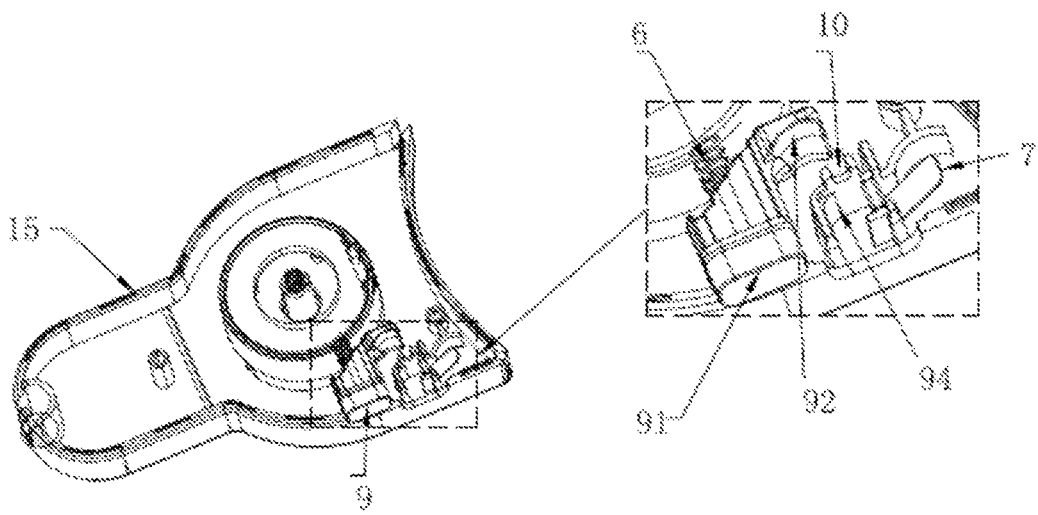
FIG. 6 is a schematic diagram of the measure tape in FIG. 5 after a tape rule is disassembled.
Figure 7:
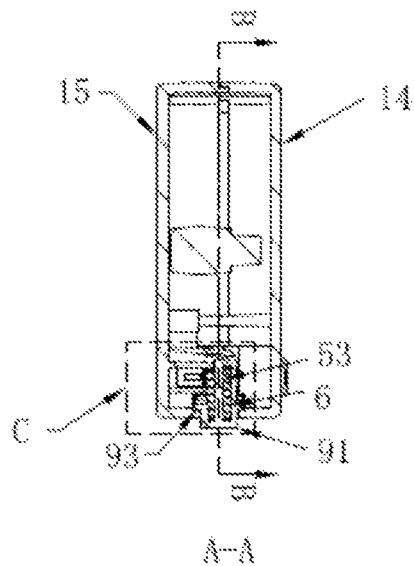
FIG. 7 is a sectional view along A-A in FIG. 4.

Reference Signs:

1, measure tape; 12, cavity; 13, shell; 14, top cover; 15, base; 16, button; 2, tape head; 3, positioning hole; 4, support plate; 5, toggle; 51, handle; 52, chuck; 53, spring plunger; 6, compression spring; 7, leaf spring; 8, tape rule; 9, key; 91, press hood; 92, chuck plate; 93, protrusion; 94, support plate; 10, notch or through hole.

DETAILED DESCRIPTION OF THE INVENTION

I. Embodiment 1

1. The structure of a measure tape 1 in this embodiment

As shown in FIG. 1-FIG. 3 and FIG. 11, a measure tape 1 for measuring the size of limbs or waists of the invention is obtained by improving an existing flexible measure tape 1, and is mainly characterized in that an elastic switch assembly is disposed on a shell 13 of the measure tape 1.

The measure tape 1 comprises the shell 13, and a cavity 12 formed in the shell 13 and used for receiving a flexible rule (also referred to as a tape rule 8), wherein the shell 13 consists of a top cover 14 and a base 15, a button 16 used for withdrawing the flexible rule into the cavity 12 is disposed on the top cover 14, and a tape head 2 is disposed at an outer end of the flexible rule.

The elastic switch assembly is disposed on one side of a positioning hole 3, and consists of a support plate 4, a toggle 5 and a compression spring 6.

(1) The support plate 4 is fixed in the cavity 12 and is formed with a notch or through hole 10, which is located behind the positioning hole 3 (with the paper direction in FIG. 1 as reference, the lower left direction is "behind", and the upper right direction is "front", the same below).

(2) The toggle 5 consists of a handle 51, a chuck 52 and a spring plunger 53.

A key hole is formed in the shell 13 on one side of the positioning hole 3, the handle 51 is disposed outside the key hole, the chuck 52 and the spring plunger 53 are disposed in the shell 13, an outer end of the chuck 52 is connected to the handle 51, the chuck 52 is a curved chuck, and the center of curvature of the chuck 52 is located behind the positioning hole 3. The design of the curved chuck is beneficial to the insertion, clamping and ejection of the tape head 2.

The spring plunger 53 is cylindrical, has a front end connected to a back side of the chuck 52, and extends backwards, and a rear end of the spring plunger 53 is disposed in the notch or through hole 10. When the handle is pulled, the rear end of the spring plunger moves backwards in the notch or through hole 10.

(3) The compression spring 6 is disposed around the spring plunger 53 and is located between the support plate 4 and the chuck 52.

(4) The measure tape of the invention is further improved in that a leaf spring 7 for applying an outward elastic force to the tape head 2 inserted into the positioning hole 3 is disposed at the bottom of the positioning hole 3.

(5) The measure tape in this embodiment is further improved in that the tape head 2 is shaped like a dumbbell which becomes larger gradually form the middle to two ends.

2. The measure tape in this embodiment is operated as follows:

(1) Measurement

A user holds the shell 13 of the measure tape 1 with one hand, holds the tape head 2 with the other hand to pull the tape rule 8 out, and then winds the tape rule 8 around a part to be measured such as the wrist; then, the user inserts the tape head 2 into the positioning hole 3 in the shell 13, and at this moment, the chuck 52 on the toggle 5 locks the tape head 2 in the positioning hole 3 under the effect of the compression spring 6; after that, the user presses the button 16 disposed on the top cover 14, and a knob spring in the cavity 12 pulls a redundant portion of the tape rule 8 back into the cavity 12, such that the tape rule 8 is tightly wound on the wrist.

The other hand of the user is freed to turn the tape rule 8 pulled out of the positioning hole 3, such that the user can observe the value at the tail end of the tape rule 8 to know the size of the wrist.

(2) Withdrawing

After measurement, the user holds the shell 13 of the measure tape 1 with one hand and pulls the handle 51 on the side face of shell 13 backwards with the other hand, such that the handle 51 drives the chuck 52 to move backwards to compress the compression spring 6; at this moment, the unlocked tape head 2 is automatically ejected out of the positioning hole 3 under the effect of an upward elastic force from the leaf spring 7; and finally, the user presses the button 16 to completely withdraw the tape rule 8 into the cavity 12.

A backward force applied to the handle 51 is released, such that handle 51 and the chuck 52 return automatically under the effect of the compression spring 6.

II. Embodiment 2

1. This embodiment is identical with Embodiment 1 except in the composition of the elastic switch assembly.

As shown in FIG. 4-FIG. 11, the elastic switch assembly is disposed on one side of the positioning hole 3, and consists of a support plate 94, a key 9 and a compression spring 6.

Figure 8:
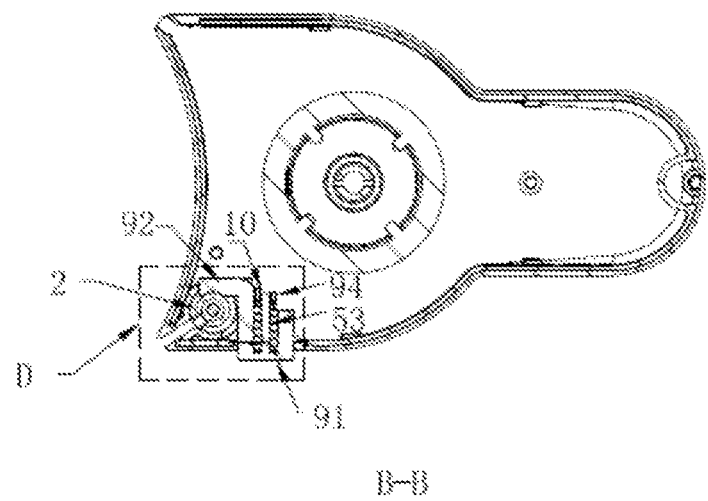
FIG. 8 is a sectional view along B-B in FIG. 7.
Figure 9:
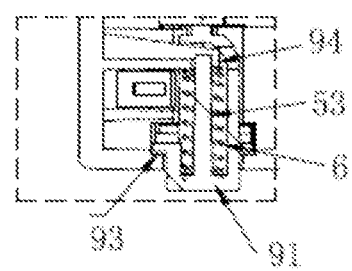
FIG. 9 is an enlarged view of part C in FIG. 7.
Figure 10:
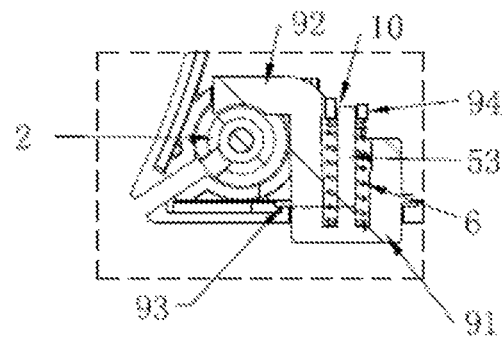
FIG. 10 is an enlarged view of part D in FIG. 8.
Figure 11:
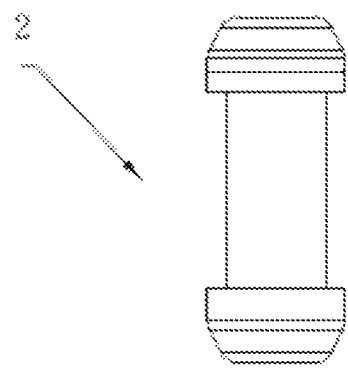
FIG. 11 is an enlarged view of a tape head.

(1) The support plate 94 is disposed in the cavity 12 and is located behind the positioning hole 3, and an inner plate is disposed on the support plate 94 and is formed with a notch or through hole 10 (with the direction in FIG. 8 as reference, the exterior of the shell is "outer", and the interior of the shell is "inner").

(2) The key 9 consists of a press hood 91, a chuck plate 92 and a spring plunger 53 which are of an integrated structure.

A key hole is formed in the shell 13 on one side of the positioning hole 3, an outer end face of the press hood 91 is a closed face, an inner end face of the press hood 91 is an open hollow cylinder, an annular protrusion 93 is disposed on the peripheral wall of the press hood 91, a portion between the protrusion 93 and the outer end face of the press hood 91 penetrates through the key hole to be disposed outside the shell 13, and the protrusion 93 is clamped in the key hole, such that the whole press hood 91 is prevented from disengaging from the key hole; the spring plunger 53 is disposed on an inner surface of an outer end in the press hood 91 and is able to extend inwards to penetrate through the notch or through hole 10, that is, an inner end of the spring plunger 53 is able to move inwards in the notch or through hole 10 after the press hood 91 is pressed.

A rear end of the chuck plate 92 is connected to the press hood 91, the chuck plate 92 is a curved plate, and the center of curvature of the chuck plate 92 is located on one side of the positioning hole 3. The design of the curved plate is beneficial to the insertion, clamping and ejection of the tape head 2.

(3) The compression spring 6 is disposed around the spring plunger 53 and is located between the inner surface of the outer end in the press hood 91 and the inner plate of the support plate 94.

(4) The measure tape in this embodiment is further improved in that a leaf spring 7 for applying an outward elastic force to the tape head 2 inserted into the positioning hole 3 is disposed at the bottom of the positioning hole 3.

2. The measure tape in this embodiment is operated as follows:

(1) Measurement

A user holds the shell 13 of the measure tape 1 with one hand, holds the tape head 2 with the other hand to pull the tape rule 8 out, and then winds the tape rule 8 on a part to be measured such as the wrist; then, the user inserts the tape head 2 into the positioning hole 3 of the shell 13, and at this moment, the chuck plate 92 on the key 9 locks the tape head 2 in the positioning hole 3 under the effect of the compression spring 6; after that, the user presses the button 16 disposed on the top cover 14, and a knob spring in the cavity 12 pulls a redundant portion of the tape rule 8 back into the cavity 12, such that the tape rule 8 is firmly wound on the wrist.

The other hand of the user is freed to turn the tape rule 8 which is pulled out of the positioning hole 3, such that the user can observe the value at the tail end of the tape rule 8 to know the size of the wrist.

(2) Withdrawing

After measurement, the user holds the shell 13 of the measure tape 1 with one hand and presses the press hood 91 inwards with the other hand, so that the press hood 91 drives the chuck plate 92 to move inwards and compress the compress spring 6; at this moment, the unlocked tape head 2 is automatically ejected out of the positioning hole 3 under the effect of an upward elastic force from the leaf spring 7; finally, the user presses the button 16 to completely withdraw the tape rule 8 into the cavity 12.

An inward force applied to the press hood 91 is released, such that the press hood 91 and the chuck plate 92 return automatically under the effect of the compression spring 6.

What is claimed is:

1. A measuring tape for measuring the size of limbs or waists, the tape measure comprising a shell, and a cavity formed in the shell and used for receiving a flexile rule, the shell comprising a top cover and a base, a button for withdrawing the flexible rule into the cavity being disposed on the top cover, a tape head being disposed at an outer end of the flexible rule, the tape head being inserted into a positioning hole in a side, opposite to a tape outlet, of the shell after being held by hand to be pulled out by a desired length via the tape outlet of the shell, wherein an elastic switch assembly for clamping the tape head in the positioning hole is disposed at a position, close to the positioning hole, in the cavity, wherein the elastic switch assembly comprises a support plate, a toggle and a compression spring, the support plate is disposed in the cavity and is located behind the positioning hole, the toggle comprising a handle, a chuck and a spring plunger which are of an integrated structure, a key hole is formed in the shell on one side of the positioning hole, the handle is disposed outside the key hole, the chuck and the spring plunger are disposed in the cavity, the chuck is a curved chuck, a center of curvature of the chuck is located behind the positioning hole, a front end of the spring plunger is connected to a back side of the chuck, a rear end of the spring plunger penetrates through and disposed in a through hole formed in the support plate, and the compression spring is disposed around the spring plunger and is located between the support plate and the chuck.

2. The measuring tape of claim 1, wherein a leaf spring for applying an outward elastic force to the tape head inserted into the positioning hole is disposed at a bottom of the positioning hole.

3. The measuring tape of claim 2, wherein the tape head is shaped like a dumbbell which becomes larger gradually from a middle to two ends.

4. A measuring tape for measuring the size of limbs or waists, the tape measure comprising a shell, and a cavity formed in the shell and used for receiving a flexile rule, the shell comprising a top cover and a base, a button for withdrawing the flexible rule into the cavity being disposed on the top cover, a tape head being disposed at an outer end of the flexible rule, the tape head being inserted into a positioning hole in a side, opposite to a tape outlet, of the shell after being held by hand to be pulled out by a desired length via the tape outlet of the shell, wherein an elastic switch assembly for clamping the tape head in the positioning hole is disposed at a position, close to the positioning hole, in the cavity, wherein the elastic switch assembly comprises a support plate, a key and a compression spring, the support plate is disposed in the cavity and is located behind the positioning hole, the key comprising a press hood, a chuck plate and a spring plunger which are of an integrated structure, a key hole is formed in the shell on one side of the positioning hole, an outer end face of the press hood is a closed face, an inner end face of the press hood is an open hollow cylinder, an annular protrusion is disposed on a peripheral wall of the press hood, a portion between the protrusion and the outer end face of the press hood penetrates through the key hole to be disposed outside the shell, the spring plunger is disposed an inner surface of an outer end in the press hood, the compression spring is disposed around the spring plunger and is located between the inner surface of the outer end in the press hood and an inner plate of the support plate, the chuck plate is a curved plate, and a center of curvature of the chuck plate is located on one side of the positioning hole.

5. The measuring tape of claim 4, wherein a leaf spring for applying an outward elastic force to the tape head inserted into the positioning hole is disposed at a bottom of the positioning hole.

* * * * *